United States Patent [19]

Rodriguez et al.

[11] 4,277,680
[45] Jul. 7, 1981

[54] NEUTRON POISON TEST DEVICE FOR HIGH DENSITY SPENT FUEL STORAGE RACKS

[76] Inventors: Luis F. Rodriguez, 1019 N. 63rd St., Philadelphia, Pa. 19151; Thomas J. Crawford, 430-B Whitman Dr., Haddonfield, N.J. 08033

[21] Appl. No.: 28,001

[22] Filed: Apr. 9, 1979

[51] Int. Cl.³ .................... G01N 23/00; G21F 5/02
[52] U.S. Cl. .............................. 250/358 R; 250/390; 250/497
[58] Field of Search .............. 250/507, 390, 391, 392, 250/358 P, 358 R, 360, 497; 176/30

[56] References Cited

U.S. PATENT DOCUMENTS

| | | | |
|---|---|---|---|
| 3,872,310 | 3/1975 | Charlton et al. | 250/358 P |
| 3,958,120 | 5/1976 | Ward | 250/321 |
| 4,038,550 | 7/1977 | Wassen et al. | 250/360 |
| 4,081,086 | 3/1978 | Shallenberger | 176/30 |

*Primary Examiner*—Alfred E. Smith
*Assistant Examiner*—Carolyn E. Fields
*Attorney, Agent, or Firm*—Paul & Paul

[57] ABSTRACT

A neutron poison test device for verifying that high density spent nuclear fuel racks contain neutron poison (a substance that absorbs neutrons without inducing a nuclear fission which produces more neutrons) comprises a can having a square cross-section, which contains a fast neutron source and neutron moderator, and four square cans each containing a thermal neutron detector, one detector can positioned opposite each of the four walls of the source can. The five cans are carried at the lower ends of five elongated tubes, which are connected together at the top by a structure having means for receiving the lifting hook of a hoist or crane. A neutron shield having a hollow square cross-section is supported for sliding movement on the center tube and is adapted to envelop the source can when the test device is outside the high density storage rack. Each of the four walls of the sliding shield contains a Boral plate or other thermal neutron absorber plate. The interior of the source can is filled with a moderating material (paraffin or water) which slows or thermalizes the neutrons. The can is partitioned to permit certain zones and layers of the moderator to be mixed with neutron absorber, thus providing shielding in desired directions, but permitting an unshielded flow of neutrons toward the detectors. Shielding prevents unnecessary radiation doses to workers using the device.

8 Claims, 9 Drawing Figures

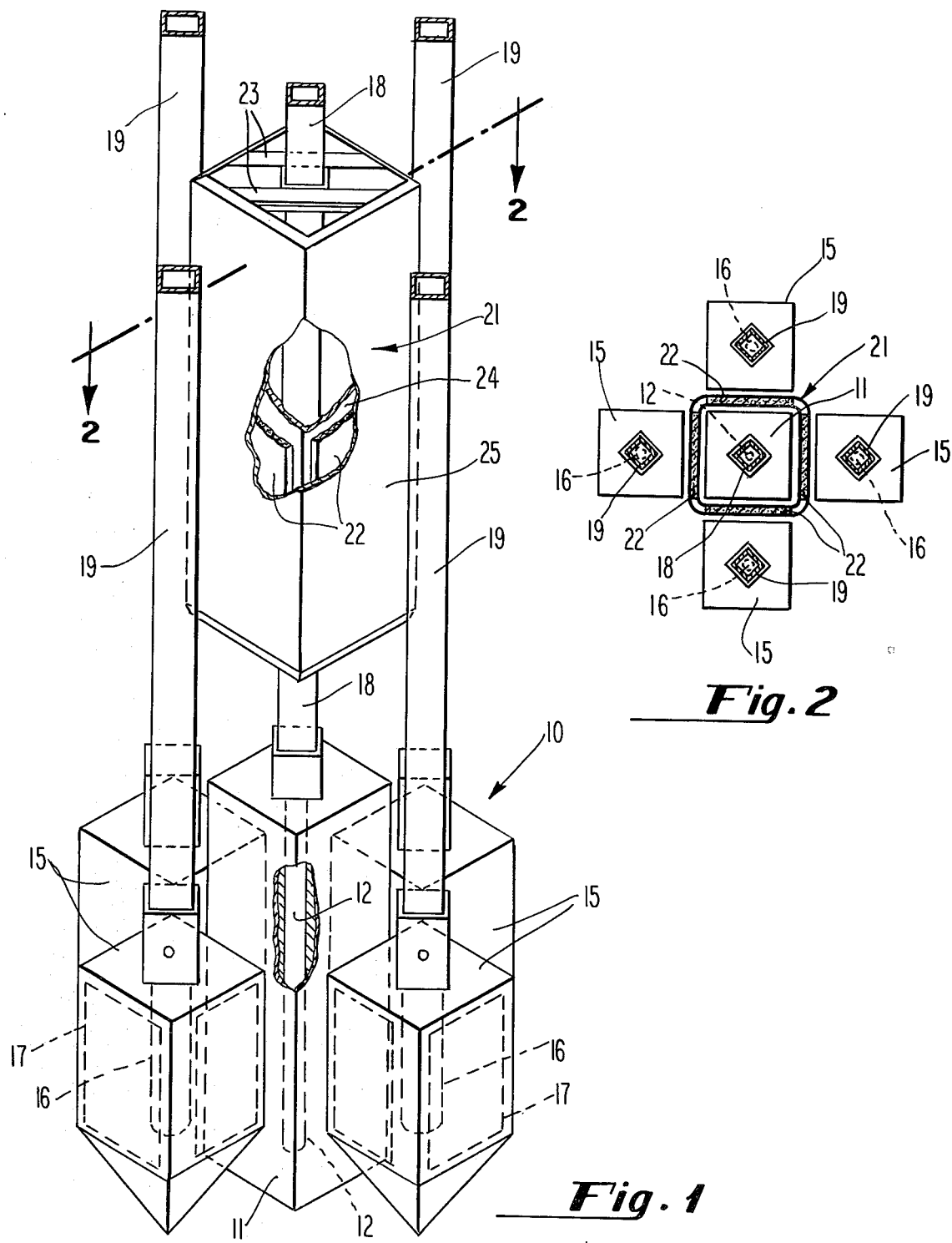

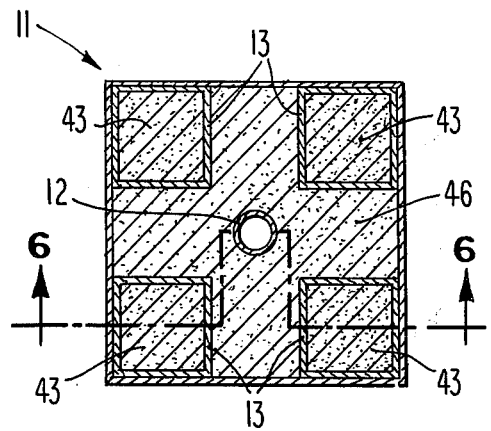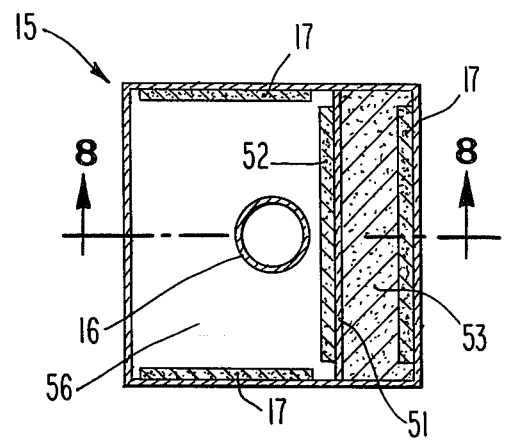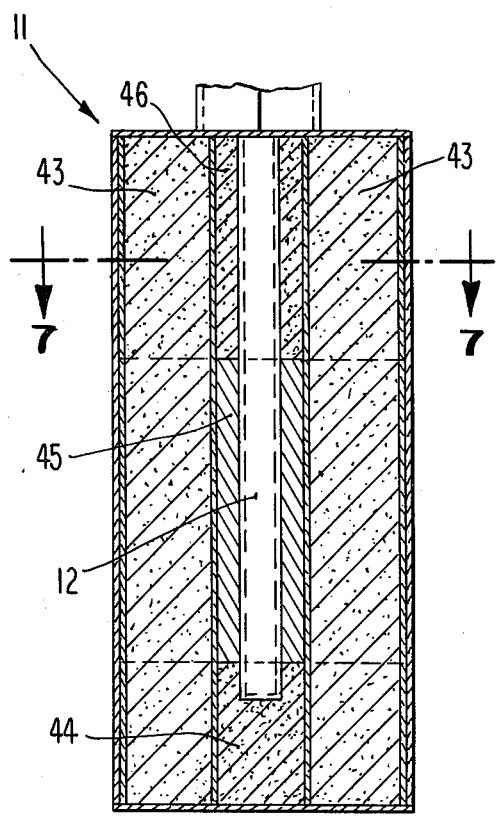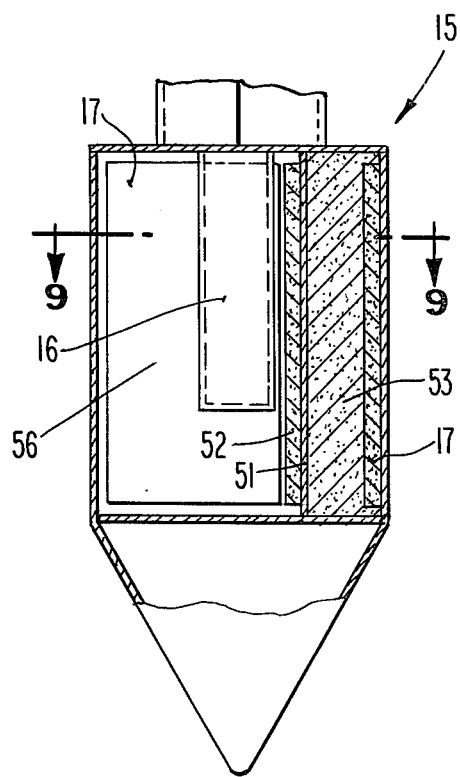

NEUTRON POISON TEST DEVICE FOR HIGH DENSITY SPENT FUEL STORAGE RACKS

BACKGROUND OF THE INVENTION

This invention is used to inspect storage racks for spent nuclear fuel before their installation and use.

One of the problems which electric power companies have to resolve when they use a nuclear reactor for generation of power is the disposition of the spent nuclear fuel. A fuel assembly may have a useful life of 4 years, at the end of which it must be replaced. Storage racks have been developed for storage of spent fuel while awaiting final shipment off site. Such racks are placed in a pool of water in the reactor building and kept completely submerged for shielding and cooling. The pool of water is so located relative to the reactor that the spent fuel assemblies may be lifted, as by a crane, and placed in one of the storage locations in the rack. Since water is an excellent shield and coolant, protection is afforded during both the removal of the spent fuel assembly from the reactor assembly and also during the storage thereof in the submerged rack.

"High density" racks differ from normal storage racks in that they use plates of a thermal neutron absorbing material between the stored fuel assembles to decrease the reactivity of the storage configuration, thus permitting closer spacing between fuel assemblies, or a higher density of storage. Therefore, the capacity of the spent fuel storage pool is increased. Because the thermal neutron absorber is crucial in preventing an accidental criticality of the closely spaced fuel within the racks, the Nuclear Regulatory Commission is requiring utilities installing these racks to verify the presence of all the thermal neutron absorber plates within these racks. Since the plates are not visible inside the racks (because they are contained between the walls of two concentric square tubes), it is necessary to perform this inspection using a neutron source and detector.

The four thermal neutron absorber plates sealed within the two concentric square tubes form a "poison can." The poison cans are placed in every other storage location of a high density rack (checkerboard fashion). When a fuel assembly is inserted into a location which has a poison can, each of the four poison plates in the poison can will be adjacent to one of the four sides of the fuel assembly. When another fuel assembly is inserted into an adjacent storage location, a poison plate lies between the two assemblies, preventing thermal neutrons from passing and, therefore, chain reaction from occurring. A material called Boral (a product of Brooks and Perkins Inc.) is often used for the poison plates. Boral is made of boron carbide powder (boron being an excellent thermal neutron absorber) dispersed in ann aluminum matrix, which is sandwiched between two sheets of thin aluminum cladding. The resulting plate is one eighth ($\frac{1}{8}$") inch thick, and four such plates approximately five and three fourths ($5\frac{3}{4}$") inches by thirteen (13') feet are sealed between two concentric square aluminum tubes, each about one eighth ($\frac{1}{8}$") inch thick, to form the above mentioned poison can. Each high density rack contains from 64 to 120 fuel storage locations in a rectangular matrix; since poison cans are only placed in alternate storage locations, a rack may contain from 32 to 60 poison cans. There are different high density rack designs which may or may not use poison cans as described herein.

SUMMARY OF THE INVENTION

The object of the present invention is to provide a test device for testing a high density storage rack to make certain, prior to storing any spent fuel assemblies therein, that alternate fuel storage cavities in a checkerboard array have poison cans each having four Boral plates, one plate at each of the four sidewalls of the poison can. In brief, before storage of any spent fuel in the rack, the test device assures that no Boral plates have been omitted. This test is a requirement of the Nuclear Regulatory Commission.

A principal purpose then of the present invention is to provide a test device which is adapted for, and capable of, testing for the presence or absence of the necessary four Boral plates in each of the poison cans of a high density fuel storage rack.

BRIEF DESCRIPTION OF THE DRAWINGS

FIG. 1 is a perspective view of the detector/ source end of a neutron poison test device according to the present invention, showing the source can (center) and surrounding detector cans, as well as the sliding shield (above the source can).

FIG. 2 is a top plan view of the neutron poison test device taken along the line 2—2 of FIG. 1.

FIG. 6 is a schematic elevational view, in section, of the source can of the test device, as seen looking along the line 6—6 of FIG. 7. The source is contained in the central tube, borated paraffin is in the corner sections and in the upper and lower layers of the central (cruciform) section, and pure paraffin in the central layer of the central (cruciform) section.

FIG. 7 is a view looking down along the line 7—7 of FIG. 6. This shows the four corner sections filled with borated paraffin, and the upper and lower layers of the central (cruciform) section, which is of borated paraffin, as well as the source containment cavity (center).

FIG. 8 is a schematic elevational view, in section, of one of the detector cans of the test device, as seen looking along the line 8—8 of FIG. 9. This shows the detector containment tube (center) and the neutron flux trap provided for shielding behind the detector.

FIG. 9 is a view looking down along the line 9—9 of FIG. 8.

DETAILED DESCRIPTION OF THE PREFERRED EMBODIMENTS

Figure 3:
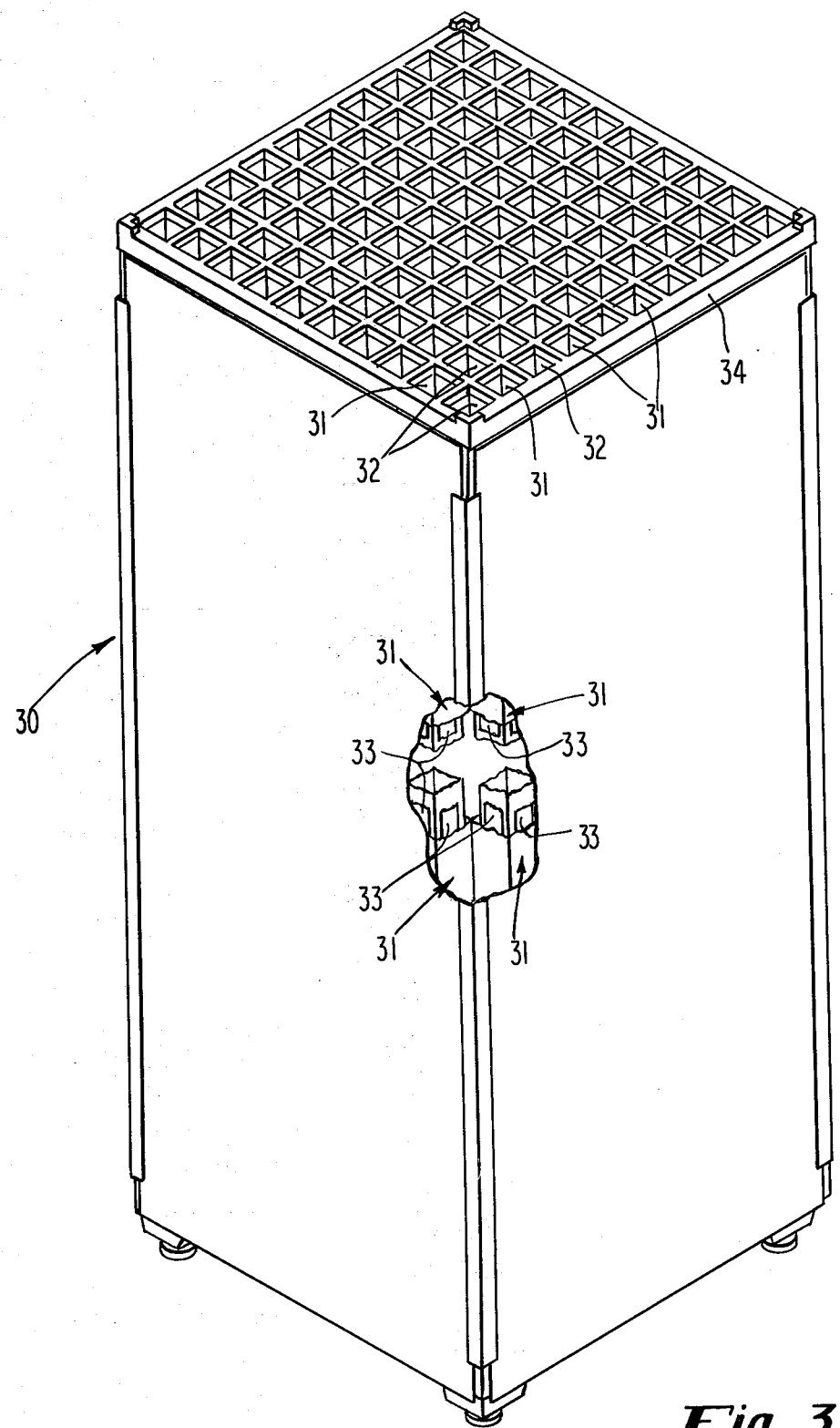
FIG. 3 is a perspective view of a high density storage rack for spent nuclear fuel of a type which may be tested by the test device of the present invention.

Reference will first be made to FIG. 3 which shows a typical high density spent nuclear fuel storage rack 30 of the type which is to be tested by the test device of the present invention. In FIG. 3, a typical storage rack 30 is shown to comprise a total of one hundred elongated tubular cavities (square in cross section) in a ten-by-ten array (these numbers may vary). Alternate cavities contain poison cans, identified by the reference numeral 31. Each poison can 31 contains four thermal neutron absorbing plates, or shields 33, typically Boral plates, one plate positioned at each of the four sidewalls of the poison can. The poison cans 31 are arranged in a checkerboard array. The alternate cavities 32 do not contain any poison cans since only one Boral plate is needed between adjacent fuel assemblies.

As has already been indicated, the function of the test device of the present invention is to make certain that each poison can 31 is equipped with four thermal neutron shielding plates 33 which hereinafter will be assumed to be Boral plates.

FIG. 1 illustrates the test device according to the present invention. As there shown, the test device 10 comprises a source can 11 containing a fast neutron source inside a small diameter tube 12 surrounded by layers and sections of (as necessary) a neutron moderator, or a neutron moderator mixed with a boron compound. The function of the neutron moderator is to slow down, or thermalize, the fast neutrons emitted by the source. The function of the borated moderator is to thermalize and absorb the neutrons, providing shielding in desired directions. The preferred modulator is paraffin. The function of the cylindrical tube 12 containing the fast neutron source is to facilitate rapid insertion and removal of the neutron source into the can 11 in order to reduce dosage that would otherwise to received from handling the bare source.

Arranged symmetrically around the fast neutron source can 11 are four detector cans 15, each containing a thermal neutron detector 16. The source can 11, and each of the four detector cans 15, are connected as by bolts, to the lower ends of elongated tubes 18, 19 to allow for the insertion of the test device fully into the elongated cavities 32 and poison cans 31 of the storage rack 30. The five elongated tubes 18,19 are connected together at the top by a structure (not shown) having an eye or other means for receiving the lifting hook of a hoist or crane.

It is required by Nuclear Regulatory Commission regulations to maintain radiation doses to personnel as low as reasonably achievable, so protection from the fast neutron source 12 is provided when the test device 10 is not yet inside the storage rack. For this purpose, a hollow square sliding shield 21 is provided. The sliding shield 21 (which is a section of a poison can) contains four Boral plates 22, one located at each of the sidewalls of the shield. The interior width of the sidewalls of the shield 21 are larger than that of the sidewalls of the neutron source can 11 to allow the shield to slide over and cover the source can 11 when the device is outside of a rack.

The cross-sectional dimensions of the fast neutron source can 11 are such that it fits slidably into any of the cavities and poison cans 31 of the storage rack 30. Since the sliding shield 21 is larger in cross sectional dimensions than the fast neutron source can 11, the sliding shield 21 cannot enter into a storage cavity 32 of storage rack. Instead, the sliding shield 21 remains on top of the storage rack 30 as the detector device 10 is progressively inserted into the elongated cavities 32 and poison cans 31 of the storage rack.

Figure 5:
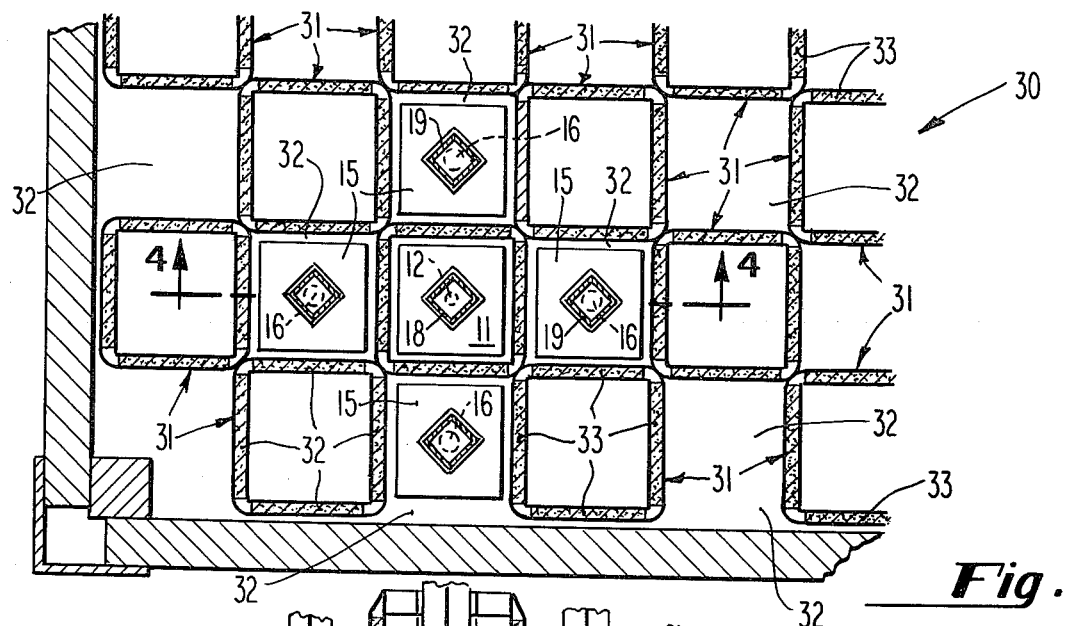
FIG. 5 is a schematic plan view, looking down along the line 5—5 of FIG. 4.

In inserting the test device into the storage rack, the source can 11 is inserted into one of the poison can storage cavities 32. Simultaneously, each of the four detector cans 15 enters one of the adjacent cavities 32. This is illustrated in FIG. 5.

Figure 4:
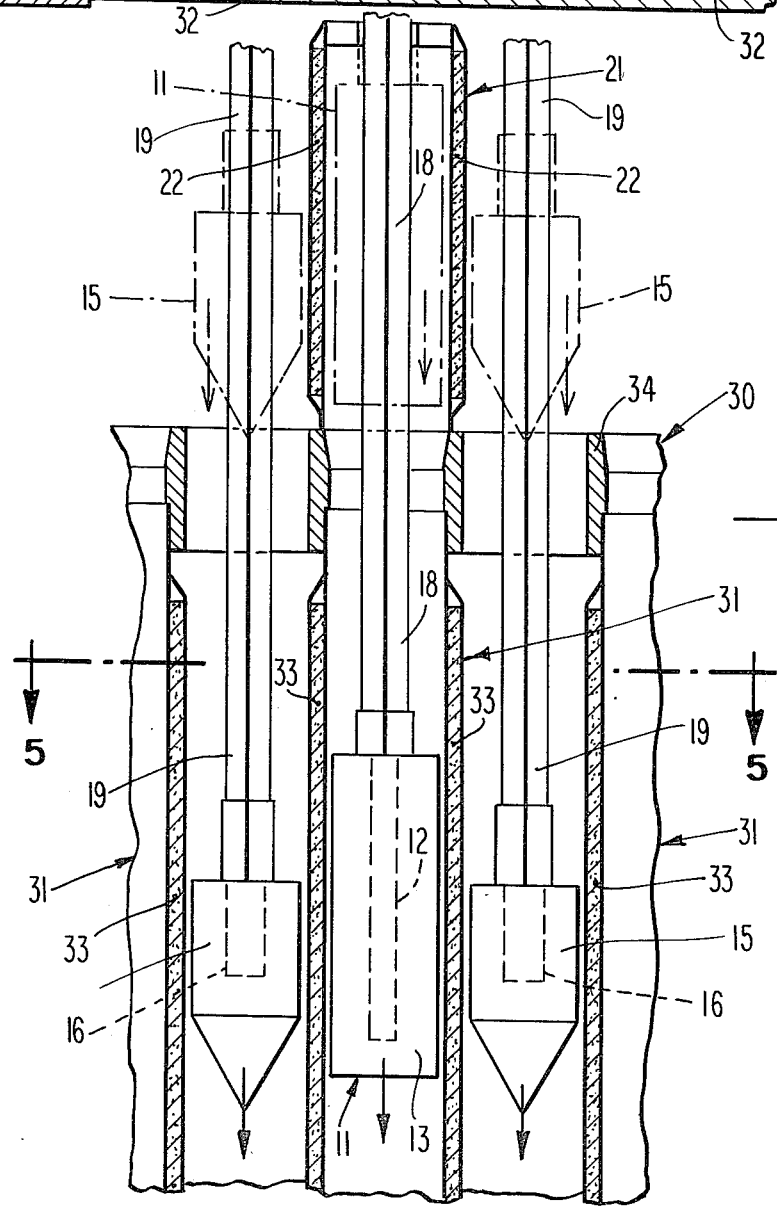
FIG. 4 is a schematic elevational view illustrating the test device of the present invention being inserted into one of the storage locations (with poison can shown in the lower portion) of the high density rack of FIG. 3, as seen looking along the line 4—4 of FIG. 5.

Immediately after the test device 10 is inserted into the top of the storage rack 30 (the sliding shield 21 remains on the top casting 34 of the rack) the source can 11 and detector cans 15 pass through the rack top casting 34 which is of short length and devoid of Boral plates. This is illustrated in FIG. 4 which shows that the Boral plates 33 in the poison cans do not extend all the way to the top surface of the rack, i.e. they do not extend through the top casting 34. Thus, as the test device passes through this short unshielded or non-poisoned length of top rack casting 34, the four thermal neutron detectors 16 count moderated neutrons from the source 12. The detector output is fed to four chart recorders, which will record a high number of counts while the device passes through the unpoisoned top casting. As the test device continues slowly down, it emerges from the top rack casting 34 and reaches the elevation of the Boral plates 33 which are excellent thermal neutron absorbers. The number of thermal neutrons from the source 12 now reaching the four detectors 16 is decreased. This is evidenced on the trace recording. This measurable decrease in signal trace (decrease by a factor of 10) will take place in all four detectors 16 provided the poison can 31 being tested is equipped with four Boral plates. If any one or more, or all, of the Boral plates is [are] missing from the poison can 31 being tested, thermal neutrons from the source can 11 will not be absorbed by a Boral plate 33, and, accordingly, one or more, or all, of the detectors 16 in the cans 15 will continue to detect a high number of counts, with a resulting high trace recording.

In summary, when the test device 10 is inserted into a particular poison can 31, signals developed by the detectors 16 in the four detector cans 15 are simultaneously recorded, and the presence or absence of Boral plates 33 at each of the four walls of the particular poison can being tested is detected for the full length of the poison can. The test device is then removed and inserted in another poison can 31 where the test just described is repeated. This is repeated (typically) fifty times as the test device is inserted into each of the fifty storage cavities 32 having poison cans 31 of the one-hundred cavity storage rack 30 illustrated in this application.

It may be pointed out that when the source can 11 of the test device is inserted into a poison can cavity 32 located adjacent an edge of the rack, one of the detector cans 15 will be outside the rack housing; and when the test device is inserted into a poison can located at a corner of the rack, two of the detector cans 15 will be outside the rack housing. This does not affect the adequacy of the test at these locations.

While not illustrated in the drawings, a shielded, portable storage system which includes a storage stand and cover, is provided for the source can 11 and sliding shield 21 when the test device is not in use. Since the source may not be left unprotected, it would normally be necessary to place the source back in its cask overnight or when not in use. Since handling of the bare source results in high personnel doses, a storage stand is provided for the source can and sliding shield to reduce the need for removal of the source from the source can. On the floor of the storage stand, which is mounted on a dolly, lies a Boral plate, and above the Boral plate the bottom section of the storage stand is filled with a borated moderator, such as borated paraffin. Just above the paraffin-filled bottom section, a perimeter ledge is provided for supporting an aluminum shelf. This shelf supports the source can 11 and sliding shield 21. The four walls of the stand are made of aluminum. After the source can 11 containing the neutron source 12, and the sliding shield 21, have been placed on the storage stand, a shielded storage cover is placed over the stand. Each of the outside sidewalls of the storage cover is covered with Boral plates, and the sidewall annulus and top portion of the storage cover are filled with a borated moderator, such as borated paraffin. The storage system provides a safe configuration for temporary storage and precludes handling of the bare source.

While not illustrated in the present application, a test stand for checking the test device is also provided. This test stand consists of an open-ended wooden or aluminum box, containing a section of poison can 3 or 4 inches shorter than the box. Because the poison can section is shorter than the box, when the test device is inserted into the stand, high counts will be recorded as the source box passes through this unpoisoned section into the poison can. As the source can enters the section of poison can, the neutron counts will decrease in the adjacent detectors. The test stand thus simulates a rack cavity, and permits confirmation that the instruments operate correctly before actual use for inspection.

While intending not to be limited to material or dimensions given below, a test device according to the invention has been completed and tested. It is an aluminum structure. The poison can housing, the detector can housing, the sliding shield, the five supporting tubes, and the cap from which the five supporting tubes are suspended, are all made of aluminum. The test device is approximately one foot square in cross section and seventeen feet (17') long. The fast neutron source can is square in cross section. It is one foot five inches (1'5") high and five and five-eighth inches (5⅝") on each side. The four detector cans are each of square cross section. Each is seven inches (7") high and five and five-eight inches (5⅝") on each side. The five supporting tubes 18, 19 are square in cross section. Each is approximately sixteen feet (16') long and one and one-half inches (1½") on each side. The neutron moderator, which surrounds the fast neutron source in the source can, is preferably paraffin, but may be water. While not shown in the drawings, means are provided for adjusting, to a limited extent, the spacing between the cans in order to allow for possible differences in spacing between rack cavities of different rack designs. The length of the device may also be varied to provide for differences in cavity depth.

As illustrated in FIG. 1, at the top of the shield 21, a pair of angle irons 23 extend diagonally between sidewalls, one angle iron on either side of the square center supporting tube 18. These angle irons stabilize the sliding shield 21 as it moves up and down on the center tube 18.

As seen in the broken-away portion of FIG. 1, and in cross-section in FIG. 2, shield 21 is constructed of an inner square aluminum tube 24 and an outer square aluminum tube 25. The two tubes 24, 25 are welded together at the top and bottom. Four Boral plates 22 are captured between the inner and outer tubes 24,25, one plate at each sidewall. The shield in the device as built is a section of poison can.

As seen in the broken-away portion of FIG. 3, and in cross-section in FIGS. 4 and 5, each poison can 31 is constructed of an inner square aluminum tube and an outer square aluminum tube. The inner and outer tubes are welded together at the top and bottom, and the four Boral plates 33 are captured between the inner and outer tubes, one plate at each sidewall. As seen in FIG. 4, the poison cans 31 are held in place by a pressure fit at the top between the upwardly extended inner square tube of the can 31 and the grid-like top casting 34, and supported at the bottom between the downwardly extended inner square tube of the can 31 and a grid-like bottom casting (not shown).

The design of the source can 11 and detector cans 15 should also be noted. The source can 11 is shown in FIGS. 6–7. One of the detector cans 15 is shown in FIGS. 8–9. Nuclear Regulatory Commission regulations require keeping personnel doses as low as reasonably achievable. Because the neutron source employed in this device could give high doses to personel, much attention has been given to personnel shielding (as with the sliding shield and the shielded storage system). Since it is only necessary to have neutrons traveling in the direction of the detectors, the source can 11 has been divided into sections to permit placement of borated moderator in the directions where neutrons are undesirable. As seen in FIGS. 6–7, each inside corner of the source can 11 a square tube 13 (dimensions 2"×2"×16¾") is provided which is filled with borated paraffin 43. The paraffin thermalizes the neutrons, and the boron absorbs the thermal neutrons, thus lowering neutron doses in those directions. In the central cruciform section of the source can 11, a bottom five inch layer of borated paraffin 44 is poured, followed by a center six inch layer of pure paraffin 45, followed by an upper six inch layer of borated paraffin 46. The effect of this sectioning and layering is to provide four appropriately sized "windows" of pure paraffin 45 directed from the source toward the four detectors, through which neutrons may travel while thermalizing.

The details of construction of the detector cans 15 are shown in FIGS. 8 and 9. Since the neutrons are no longer necessary once they travel past the detectors, each of three sidewalls of detector can 15 (except the sidewall which faces one of the windows of the source can 11) is provided with a Boral plate 17. An aluminum wall 51 is provided inside the detector can 15 in the position shown in FIGS. 8 and 9, and an additional Boral plate 52 is mounted on the aluminum wall 51. The cavity 53 defined by the aluminum wall 51 is filled with a moderator, preferably borated paraffin. The center hole for the detector device 16 is, of course, not filled with a moderator. Space 56 is free of moderator to allow neutrons from the source can 11 to reach the detector 16.

The two Boral plates 17 and the cavity filled with borated moderator 53 behind the detectors form what is known as a flux trap. Thermal neutrons are absorbed mostly by the initial Boral plate. Fast neutrons pass the initial Boral plate, but are thermalized by the moderator in the cavity 53 behind it, then absorbed either by the boron mixed in the moderator or by either of the Boral plates in front and back of the cavity. In should be noted that the storage system mentioned above also provides a highly effective flux trap storage configuration.

Finally, both the detector and source cans are of cross sectional dimensions slightly larger than a fuel assembly. Therefore, as the device is inserted into a rack, a dimensional inspection is performed to provide assurance that shipping or other damage has not so distorted the cavities and/or poison cans that they will not accept an object the size of a fuel assembly.

What is claimed is:

1. A neutron poison-can test device for determining whether the storage cavities of highdensity spent nuclear fuel storage racks contain neutron poison, said test device comprising:

a. a neutron source can comprising;
- a-1 a source can housing having a square cross-section and size corresponding to but sufficiently smaller than that of the storage cavities of said storage racks to permit insertion of said can into said cavities;
- a-2 a source of neutrons contained within said source-can housing; and a sectioned and layered arrangement of neutron moderating material and borated neutron moderating material as required for moderation and shielding, forming four windows of limited size leading to the four sidewalls of the source can;
- a-3 a cylindrical tube for containing the neutron source and facilitating rapid removal and insertion of the source in order to reduce doses that would be received from handling the bare source;

b. a shield slidable over said source can, said shield comprising:
- b-1 a housing having a hollow square cross-section and having a size sufficiently larger than that of said source can to allow said shield to slide over said source can; and
- b-2 four thermal neutron shielding plates, held in the hollow portion of said housing, one located against each of the four walls of said shield housing, thereby to inhibit penetration of neutrons through said shield housing;

c. four detector cans symmetrically disposed about said source can, each of said detector cans comprising;
- c-1 a can housing having a square cross section and size corresponding to but sufficiently smaller than said cavities of said storage racks to permit insertion of said can into said cavities;
- c-2 a thermal neutron detector contained in a tube mounted within said can; and
- c-3 thermal neutron absorbing material at all sidewalls of the detector can except the sidewall facing said source can;

d. a plurality of five elongated tubes for individually supporting said source can and four detector cans at the lower ends of said tubes in such configuration that when said source can is inserted into the upper end of a storage cavity of said storage rack, the four detector cans enter the four cavities adjacent to said cavity, said slidable source-can shield being prevented from entering into said cavity because of its larger size, said slidable shield remaining on the upper surface of said storage rack as said test device is lowered through said cavity and the four cavities adjacent thereto.

2. A test device according to claim 1 wherein said thermal neutron shielding plates of said shield are Boral plates, and the shield as a whole is a section of poison can.

3. A test device according to claim 2 wherein said neutron source can has borated moderator material at each of the four corners of said can also at the bottom and top of the can for shielding, with a center layer of pure moderator material at the center of the can.

4. A test device according to claim 3 wherein said detector can is provided with a plate of thermal neutron absorbing material or Boral plate at each sidewall except the sidewall which faces said source can.

5. A test device according to claim 4 wherein an aluminum separator is provided within the detector can forming a chamber within the can adjacent the sidewall which is opposite to and most remote from said source can, and wherein said chamber is filled with a borated moderator.

6. A test device according to claim 5 wherein a Boral plate is fixed to said separator.

7. A test device according to claim 3 wherein said source of neutrons in said source-can housing is a source of fast neutrons.

8. A neutron poison-can test device for testing storage cavities of a high-density spent nuclear fuel storage rack for presence or absence of thermal neutron shielding material a. a neutron source can comprising;
- a-1 a housing having a cross-sectional shape and size corresponding to but sufficiently smaller than that of storage cavities of said storage racks to permit insertion of said cans into said cavities;
- a-2 a source of fast neutrons contained within said housing;
- a-3 a cylindrical tube for containing the neutron source and for facilitating rapid removal and insertion of the source in order to reduce doses otherwise received from handling the bare source; and
- a-4 borated moderator material surrounding said fast neutron source except for four windows or pure moderator material of limited area leading to the four sidewalls of the housing of said source can;

b. a shield slidable over said fast neutron source can, said shield comprising;
- b-1 a housing having a hollow square cross-sectional shape and size corresponding to but sufficiently larger than that of said neutron source can to allow said shield to slide over said source can, said housing including an inner square tube and an outer square tube welded together at top and bottom;
- b-2 four thermal neutron shielding plates captured between said inner and outer tubes, one located against each of the four walls of said shield housing, for inhibiting penetration of neutrons through said shield housing;

c. four detector cans symmetrically disposed about said source can, each of said detector cans comprising:
- c-1 a housing having a cross-sectional shape and size corresponding to but sufficiently smaller than that of said cavities of said storage racks to permit insertion of said housing into said cavities;
- c-2 a neutron detector contained within said detector can; and
- c-3 neutron moderator and absorber material surrounding said neutron detector except for a window leading to the sidewall of said detector-can housing facing one of said windows of said source can;

d. a plurality of five elongated tubes for supporting individually said source can and four detector cans at the lower ends of said tubes in such configuration that, when said source can is inserted into the upper end of a storage cavity of said storage rack, the four detector cans enter the four storage cavities adjacent to said storage cavities, said slidable shield, because of its larger cross sectional dimensions, being prevented from entering into said storage cavity, said slidable shield remaining on the upper surface of said storage rack as said test device is lowered through said cavity and the four cavities adjacent thereto.

* * * * *